United States Patent
Kumagai et al.

(10) Patent No.: US 7,910,876 B2
(45) Date of Patent: Mar. 22, 2011

(54) PLANT SENSOR

(75) Inventors: Kaoru Kumagai, Itabashi-ku (JP); Shugo Akiyama, Itabashi-ku (JP)

(73) Assignee: Kabushiki Kaisha Topcon, Tokyo (JP)

( * ) Notice: Subject to any disclaimer, the term of this patent is extended or adjusted under 35 U.S.C. 154(b) by 0 days.

(21) Appl. No.: 12/461,803

(22) Filed: Aug. 25, 2009

(65) Prior Publication Data

US 2010/0053628 A1   Mar. 4, 2010

(30) Foreign Application Priority Data

Aug. 29, 2008 (JP) ................. 2008-221625

(51) Int. Cl.
*G01N 21/27* (2006.01)
*A61G 7/00* (2006.01)

(52) U.S. Cl. .................... 250/226; 250/341.8
(58) Field of Classification Search ............... 250/226, 250/341.1, 341.8, 358.1
See application file for complete search history.

(56) References Cited

U.S. PATENT DOCUMENTS

| | | | |
|---|---|---|---|
| 4,986,665 A | 1/1991 | Yamanishi et al. | |
| 5,389,781 A | 2/1995 | Beck et al. | |
| 6,008,756 A * | 12/1999 | Boerhave et al. | 342/357.13 |
| 6,160,902 A | 12/2000 | Dickson et al. | |
| 6,596,996 B1 | 7/2003 | Stone et al. | |
| 2005/0098713 A1 | 5/2005 | Holland | |
| 2010/0039804 A1* | 2/2010 | Budde et al. | 362/231 |
| 2010/0053628 A1* | 3/2010 | Kumagai et al. | 356/448 |

OTHER PUBLICATIONS

European Search Report issued Dec. 17, 2009 in EP 09 01 1043.

* cited by examiner

*Primary Examiner* — John R Lee
(74) *Attorney, Agent, or Firm* — Wenderoth, Lind & Ponack, L.L.P.

(57) ABSTRACT

A plant sensor includes a light source section having first and second light emitters configured to irradiate first and second measuring light toward an object to be measured, respectively, and a light receiver configured to receive reflected light from the object to be measured, and output light-receiving signals. A controller is configured to control emission of the first and second light emitters at a different timing, an integrator is configured to integrate the light-receiving signals, and output an integration signal, and a calculator is configured to calculate, according to the integration signal, a reflection rate as a ratio of light intensity of the reflected light of the first measuring light from the object to be measured to light intensity of the first measuring light, a reflection rate as a ratio of light intensity of the reflected light of the second measuring light from the object to be measured to light intensity of the second measuring light, and to obtain information regarding a growing condition of the object to be measured.

11 Claims, 9 Drawing Sheets

PLANT SENSOR

PRIORITY CLAIM

The present application is based on and claims priority from Japanese Patent Application No. 2008-221625, field on Aug. 29, 2008, the disclosure of which is hereby incorporated in its entirety.

BACKGROUND OF THE INVENTION

1. Field of the Invention

The present invention relates to a plant sensor capable of determining a growing condition of a crop or the like by irradiating measuring light toward the crop or the like of an object to be measured, and measuring the light intensity of the reflected light from the crop or the like. In particular, it relates to an improvement in a plant sensor capable of determining a growing condition of a crop or the like by obtaining a reflection rate according to the light intensity of the reflected light.

2. Description of the Related Art

In recent years, farmland areas have been decreasing due to changes in the environment, while the world's population has been increasing. Accordingly, farmland area per unit of the population has been decreasing, and it has been noted that the decrease in the farmland area per unit of the population will likely result in a food crisis.

Consequently, it has been requested to improve the production capacity of a crop per unit area, such as grains and vegetables. For this reason, it is important to accurately determine the growing condition of a crop, so as to effectively produce the crop.

Heretofore, an agricultural sensor such as a plant sensor has been proposed for determining a growing condition of a crop.

Figure 1A:
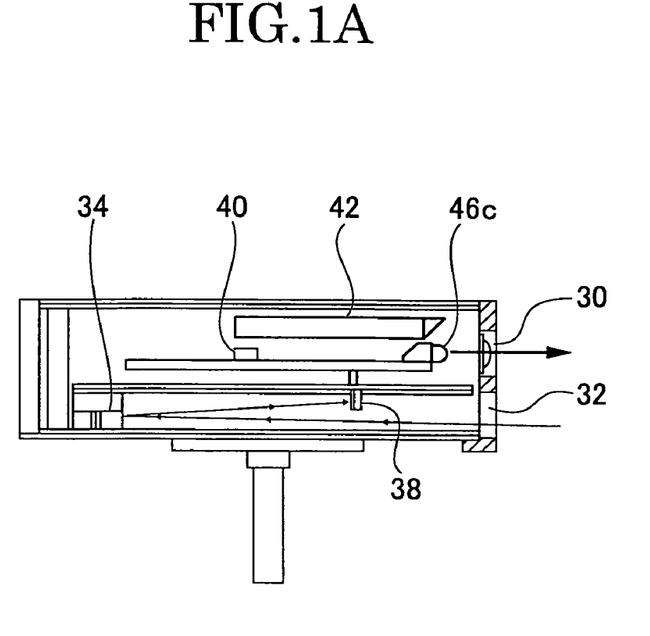
FIG. 1A provides a longitudinal sectional view illustrating a light source of a conventional agricultural sensor.
Figure 1B:
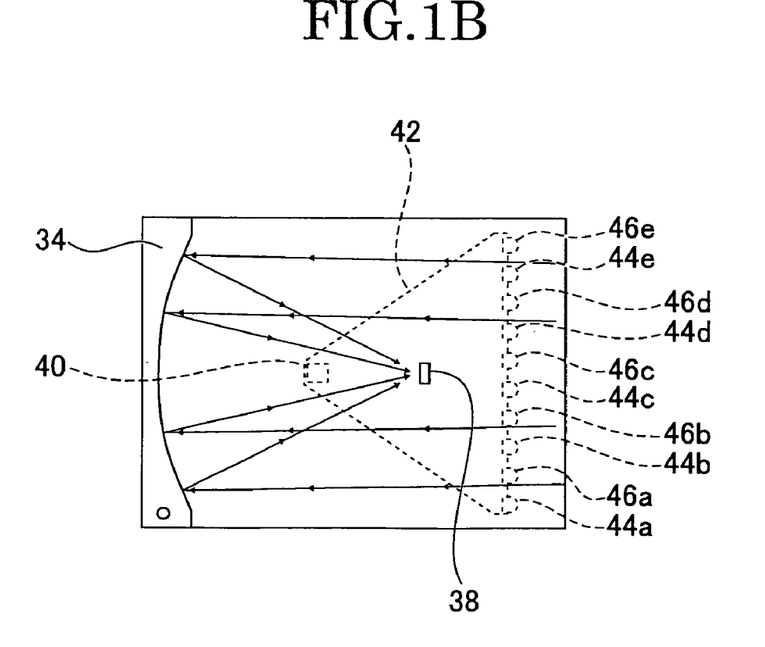
FIG. 1B provides a plan view illustrating the light source of the conventional agricultural sensor.

FIGS. 1A, 1B illustrate a general structure of a light source of a conventional agricultural sensor. In this agricultural sensor, the measuring light emitted from LEDs 44a-44e is irradiated to a crop, which is an object to be measured regarding a growing condition (hereinafter, referred to as an object to be measured), through a lens 30, and the light reflected from the crop is received by a first light receiver 38 via a concave mirror 34.

Moreover, in this agricultural sensor, part of the measuring light emitted from each of the LEDs 44a-44e is guided to a second light receiver 40 by a light-conductive plate 42, so as to be received by the second light receiver 40. This agricultural sensor measures the reflection rate of the crop according to the light-receiving signals of the first light receiver 38 and the light-receiving signals of the second light receiver 40.

This agricultural sensor also measures the reflection rate of the crop by using LEDs 46a-46e which emit measuring light whose wavelength is different from the wavelength of the measuring light emitted from the LEDs 44a-44e.

The conventional agricultural sensor obtains a normalization difference vegetation index (NDVI) according to the reflection rates of the two wavelengths which are different from each other (for example, refer to U.S. Pat. No. 6,596,996B1, registration date Jul. 22, 2003).

According to the conventional agricultural sensor, fertilizer can be effectively spread by obtaining the information regarding the growing condition of the crop.

By the way, in the conventional agricultural sensor, the light intensity received by the first light receiver 38 contains a component resulting from ambient light and a component according to the measuring light reflected from a crop.

In this conventional agricultural sensor, the component resulting from the ambient light is eliminated by means of a band-pass filter 32.

However, in this conventional agricultural sensor, the structure of the optical system is slightly complicated, and also the component resulting from the ambient light can not be completely eliminated even if the band-pass filter is used. Therefore, it becomes difficult to accurately measure the reflection rate of the crop.

In this conventional agricultural sensor, since the wavelength and the light-emitting intensity of the light source are changed depending on an environmental temperature, it is difficult to accurately measure the reflection rate of the crop.

SUMMARY OF THE INVENTION

It is, therefore, an object of the present invention to provide a plant sensor which can reduce an influence of a component resulting from ambient light while simplifying a structure, and can further accurately measure a reflection rate of an object to be measured while simplifying a structure.

In order to achieve the object of the present invention, a first aspect of the present invention relates to a plant sensor, including: a light source section, having: a first light emitter configured to periodically emit first measuring light whose peak wavelength of emission intensity is a first wavelength, and irradiate the first measuring light toward an object to be measured; a second light emitter configured to periodically emit second measuring light whose peak wavelength of emission intensity is a second wavelength, and irradiate the second measuring light toward the object to be measured; and a light receiver configured to receive reflected light of each of the measuring light from the object to be measured, and output light-receiving signals. In addition, the plant sensor includes a controller configured to control emission of the first light emitter and emission of the second light emitter at a different timing; an integrator configured to integrate the light-receiving signals, and output an integration signal; and a calculator configured to calculate, according to the integration signal from the integrator, a reflection rate as a ratio of light intensity of the reflected light of the first measuring light from the object to be measured to light intensity of the first measuring light, a reflection rate as a ratio of light intensity of the reflected light of the second measuring light from the object to be measured to light intensity of the second measuring light, and obtain information regarding a growing condition of the object to be measured.

A second aspect of the present invention relates to a plant sensor, including: a light source section, having: a first light emitter configured to periodically emit first measuring light whose peak wavelength of emission intensity is a first wavelength and irradiate the first measuring light toward an object to be measured; a second light emitter configured to periodically emit second measuring light whose peak wavelength of emission intensity is a second wavelength and irradiate the second measuring light toward the object to be measured; a light receiver configured to receive reflected light of each of the measuring light from the object to be measured and output light-receiving signals; and a first auxiliary light receiver configured to receive part of the first measuring light irradiated from the first light emitter. In addition, the plant sensor includes a controller configured to control emission of the first light emitter and emission of the second light emitter at a different timing; an integrator configured to integrate the light-receiving signals, and output an integration signal; and a calculator configured to calculate, according to the integration signal from the integrator and a light-receiving signal from the first auxiliary light receiver, a reflection rate as a ratio of light intensity of the reflected light of the first measuring light from the object to be measured to light intensity of the first measuring light, and obtain information regarding a growing condition of the object to be measured.

BRIEF DESCRIPTION OF THE DRAWINGS

The accompanying drawings are included to provide a further understanding of the invention, and are incorporated in and constitute a part of this specification. The drawings illustrate an embodiment of the invention and, together with the specification, serve to explain the principle of the invention.

FIGS. 8A, 8B, 8C provide an explanatory view illustrating one example of integration of light-receiving signals shown in FIG. 3, wherein FIG. 8A illustrates the relationship between the output of the periodic pulse illustrated in FIG. 7 and the light-receiving output from the light receiver, FIG. 8B illustrates when the light-receiving output is sampled by dividing the light-receiving output into each interval, and FIG. 8C illustrates when the peak value of the light-receiving output is obtained by adding each sampling value for each interval.

DETAILED DESCRIPTION OF THE PREFERRED EMBODIMENT

Hereinafter, an embodiment of a plant sensor according to the present invention will be described with reference to the drawings.

Figure 2:
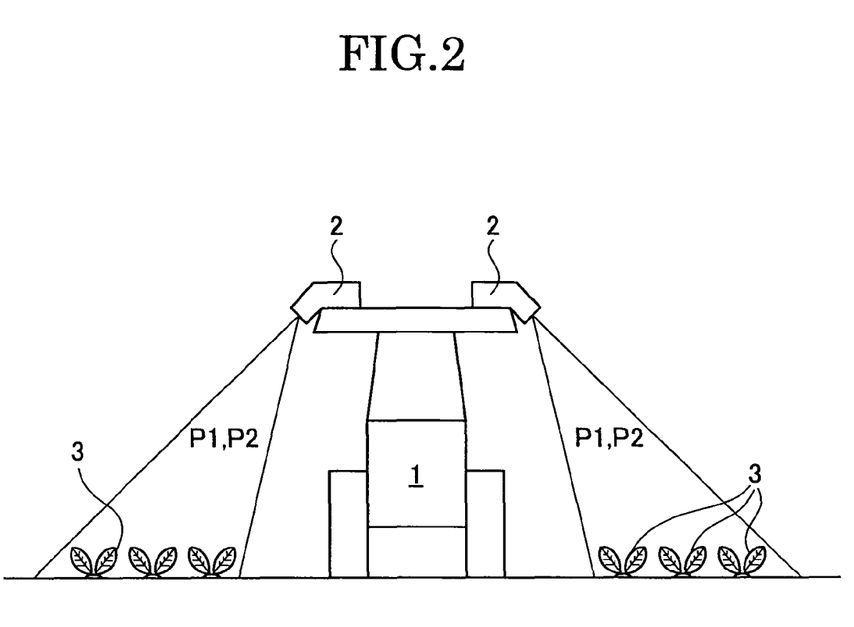
FIG. 2 provides an overall view illustrating a schematic structure of an agricultural machine to which a plant sensor according to an embodiment of the present invention is applied.

FIG. 2 provides an overall view illustrating a schematic structure of an agricultural machine to which an agricultural sensor as a plant sensor according to an embodiment of the present invention is applied.

This agricultural machine is a tractor, for example. This tractor is provided with a fertilizer spreader, for example. Agricultural sensors 2, 2 are disposed on the top of a tractor body 1 on the right and left, respectively.

Each of the agricultural sensors 2, 2 irradiates toward, for example, vegetables 3 as an object to be measured regarding a growing condition (hereinafter, referred to as an object to be measured 3) first measuring light P1 and second measuring light P2 whose peak wavelengths of emission intensity are different from each other.

Each of the agricultural sensors 2 receives the reflected light of the measuring light P1, P2 from the object to be measured 3, and measures the light intensity and the reflection rate of the reflected light. The agricultural sensors 2, 2 are used for obtaining the information regarding the growing condition of the object to be measured 3.

The information regarding the growing condition is, for example, the amount of nutrient contained in the vegetables. The amount of fertilizer which is spread by the fertilizer spreader is controlled according to the amount of nutrient.

Figure 3:
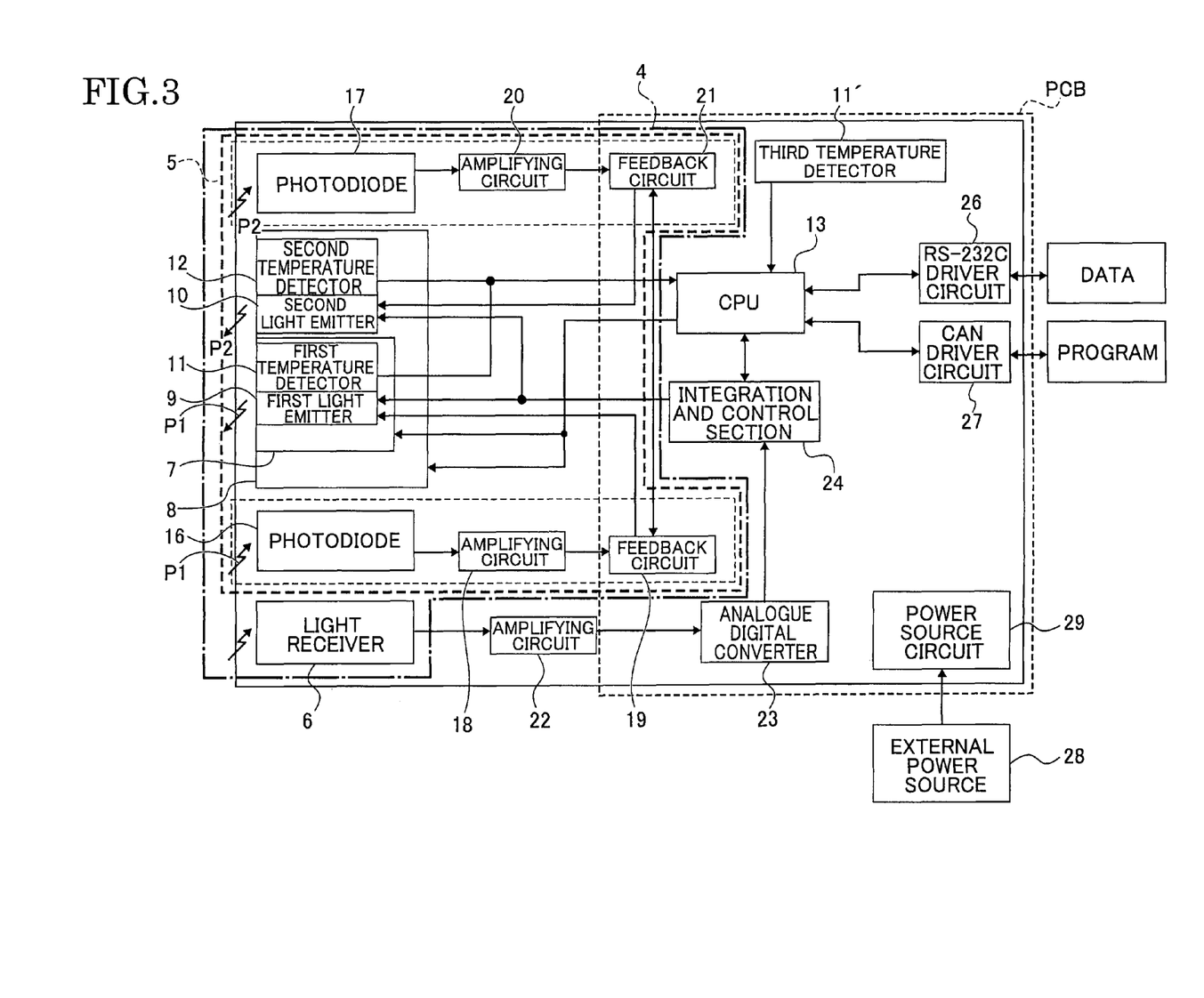
FIG. 3 provides a schematic view illustrating a circuit structure of the plant sensor.

Each of the agricultural sensors 2, 2 includes a light source section 4 as illustrated in FIG. 3. The light source section 4 includes a light-emitting unit 5 and a light receiver 6.

Figure 4:
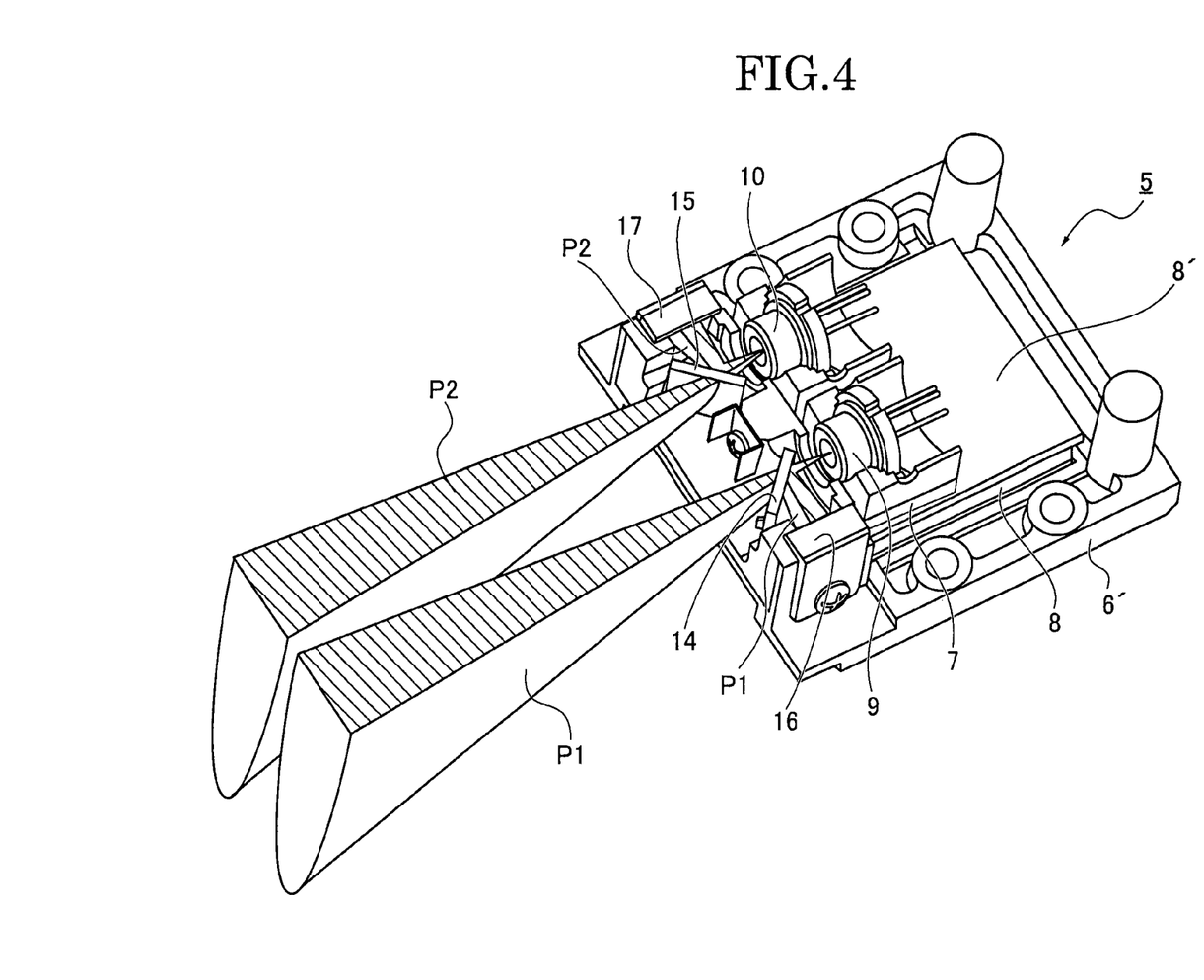
FIG. 4 provides a perspective view illustrating a detailed structure of a light-emitting unit illustrated in FIG. 3.

As illustrated in FIG. 4, the light-emitting unit 5 includes a substrate 6', a printed circuit board PCB, a first temperature adjuster 7, a second temperature adjuster 8, a pulsed oscillation laser diode (PLD) as a first light emitter 9, and a pulsed oscillation laser diode (PLD) as a second light emitter 10. The first light emitter 9 irradiates pulsed laser light whose peak wavelength of emission intensity is 733 nm (a first wavelength) toward the object to be measured 3 as the first measuring light P1. The second light emitter 10 irradiates pulsed laser light whose peak wavelength of emission intensity is 808 nm (a second wavelength) toward the object to be measured 3 as the second measuring light P2.

In this embodiment, the second light emitter 10 is disposed on the substrate 6' via a metal plate 8' and the second temperature adjuster 8, and the first light emitter 9 is disposed on the substrate 6' via the first temperature adjuster 7, the metal plate 8', and the second temperature adjuster 8. A Peltier effect element is used for each of the first temperature adjuster 7 and the second temperature adjuster 8.

As illustrated in FIG. 3, the light-emitting unit 5 includes a thermistor as a first temperature detector 11 which detects the temperature of the first emitter 9, a thermistor as a second temperature detector 12 which detects the temperature of the second emitter 10, and a thermistor as a third temperature detector 11' which detects the temperature of the printed circuit board PCB.

As illustrated in FIG. 3, the detection output of the first, second, and third temperature detectors 11, 12, 11' are input to a central processing unit 13 (hereinafter, referred to as a CPU 13). This CPU 13 mainly includes a function as a first temperature control circuit which controls the first temperature adjuster 7 according to the detected temperature result of the first temperature detector 11 such that the temperature of the first light emitter 9 becomes constant, and also includes a function as a second temperature control circuit which controls the second temperature adjuster 8 according to the detected temperature result of the second temperature detector 12 such that the temperature of the second light emitter 10 becomes constant. In this case, the second temperature adjuster 8 has a function which adjusts the temperature of the first light emitter 9 via the first temperature adjuster 7, and also directly adjusts the temperature of the second light emitter 10.

Figure 5:
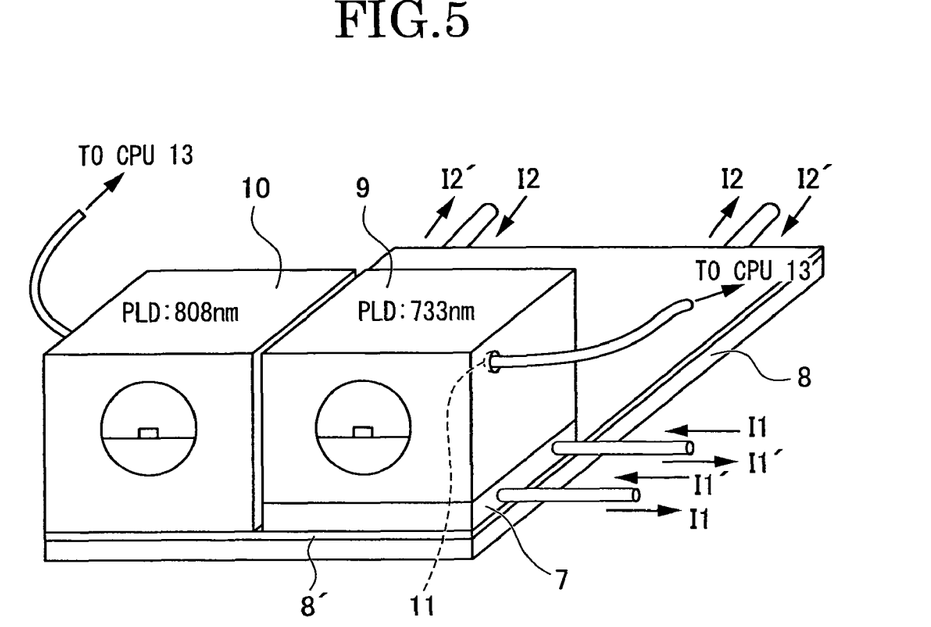
FIG. 5 provides a perspective view illustrating a general idea of temperature control by temperature adjusters illustrated in FIG. 4.

FIG. 5 illustrates a schematic view of the temperature adjustment of the first and second light emitters 9, 10 by the first and second temperature adjusters 7, 8.

If current flows through the second temperature adjuster 8 in the direction of arrow 12, the first light emitter 9 is heated via the first temperature adjuster 7 by the heat release of the second temperature adjuster 8, while the second light emitter 10 is directly heated by the heat release of the second temperature adjuster 8. On the other hand, if current flows through the second temperature adjuster 8 in the direction of the arrow 12', the first light emitter 9 is cooled via the first temperature adjuster 7 by the heat absorption of the second temperature adjuster 8, while the second light emitter 10 is directly cooled by the heat absorption of the second temperature adjuster 8.

If current flows through the first temperature adjuster 7 in the direction of the arrow I1, the first light emitter 9 is heated by the heat release of the first temperature adjuster 7, whereas if current flows through the first temperature adjuster 7 in the direction of the arrow I1', the first light emitter 9 is cooled by the heat absorption of the first temperature adjuster 7.

As illustrated in FIG. 4, the light-emitting unit 5 includes glass plates 14, 15 disposed in the traveling directions of the measuring light P1, P2 irradiated from the light emitters 9, 10, respectively. The plate glass 14 has a function of largely transmitting the measuring light P1 toward the object to be measured 3, and reflecting the remaining part of the measuring light P1. The glass plate 15 also has a function of largely transmitting the measuring light P2 toward the object to be measured 3, and reflecting the remaining part of the measuring light P2. The light-emitting unit 5 includes photodiodes 16, 17 disposed in the reflection directions of the measuring light P1, P2, respectively.

As illustrated in FIG. 3, the detection output of the photodiode 16 is amplified by an amplifying circuit 18, and is input to a feedback circuit 19. The detection output of the photodiode 17 is amplified by an amplifying circuit 20, and is input to a feedback circuit 21.

The photodiode 16 functions as a first auxiliary light receiver which receives part of the measuring light P1 irradiated toward the object to be measured 3 from the first light emitter 9. The amplifying circuit 18 and the feedback circuit 19 function as a first light intensity controller which controls the light-emitting intensity of the measuring light P1 according to the light-receiving signal from the first auxiliary light receiver such that the light intensity of the measuring light P1 of the first light emitter 9 becomes constant.

The photodiode 17 functions as a second auxiliary light receiver which receives part of the measuring light P2 irradiated toward the object to be measured 3 from the second light emitter 10. The amplifying circuit 20 and the feedback circuit 21 function as a second light intensity controller which controls the light-emitting intensity of the measuring light P2 according to the light-receiving signal from the second auxiliary light receiver such that the measuring light P2 of the second light emitter 10 becomes constant.

Figure 6:
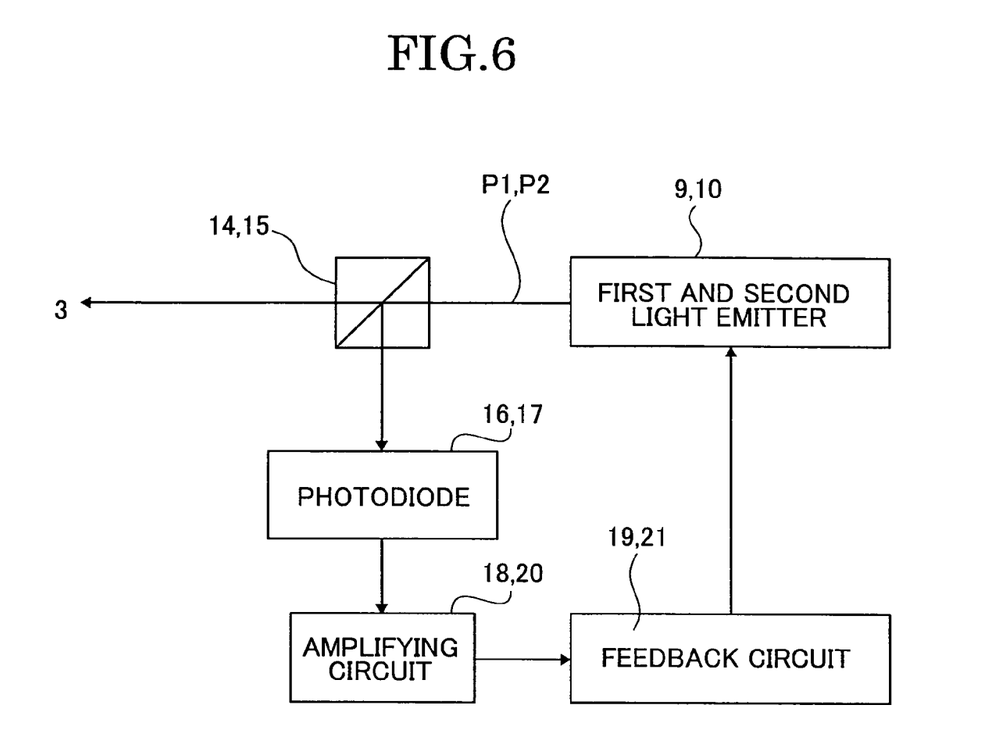
FIG. 6 provides a pattern view illustrating a general idea of control of light-emitting intensity of light emitters illustrated in FIG. 4.

More particularly, as illustrated in FIG. 6, the first and second measuring light P1, P2 emitted from the first and second light emitters 9, 10 is largely transmitting the glass plates 14, 15 and is guided to the object to be measured 3, respectively. Part of the measuring light P1, P2 is reflected by the glass plates 14, 15, and is guided to the photodiodes 16, 17, respectively. The photodiodes 16, 17 convert the reflected light into electricity, so as to output the light-receiving signal toward the amplifying circuits 18, 20, respectively.

The amplifying circuits 18, 20 output the light-receiving signal toward the feedback circuits 19, 21, respectively. The feedback circuits 19, 21 control the driving current of the first and second light emitters 9, 10 such that the sizes of the light-receiving signals become constant, respectively. Thereby, the sizes (power) of the light-emitting intensities of the measuring light P1, P2 irradiated from the first and second light emitters 9, 10 are automatically controlled to become constant. The detailed structure thereof will be described later.

The light receiver 6 receives the reflected light of the measuring lights P1, P2 from the object to be measured 3 and the ambient light. The light-receiving signals of the light receiver 6 are input to an analogue digital converter (A/D converter) 23 via the amplifying circuit 22. The A/D converter 23 converts the light-receiving signals into digital signals corresponding to the sizes of the light-receiving signals. The digital signals are input to an integration and control section (FPGA) 24.

The integration and control section (FPGA) 24 includes an integrator which integrates the light-receiving signals of the light receiver 6 in a predetermined time, and outputs the integration signal, and a controller which controls the emission of the first light emitter 9 and the emission of the second light emitter 10 at a different timing.

Figure 7:
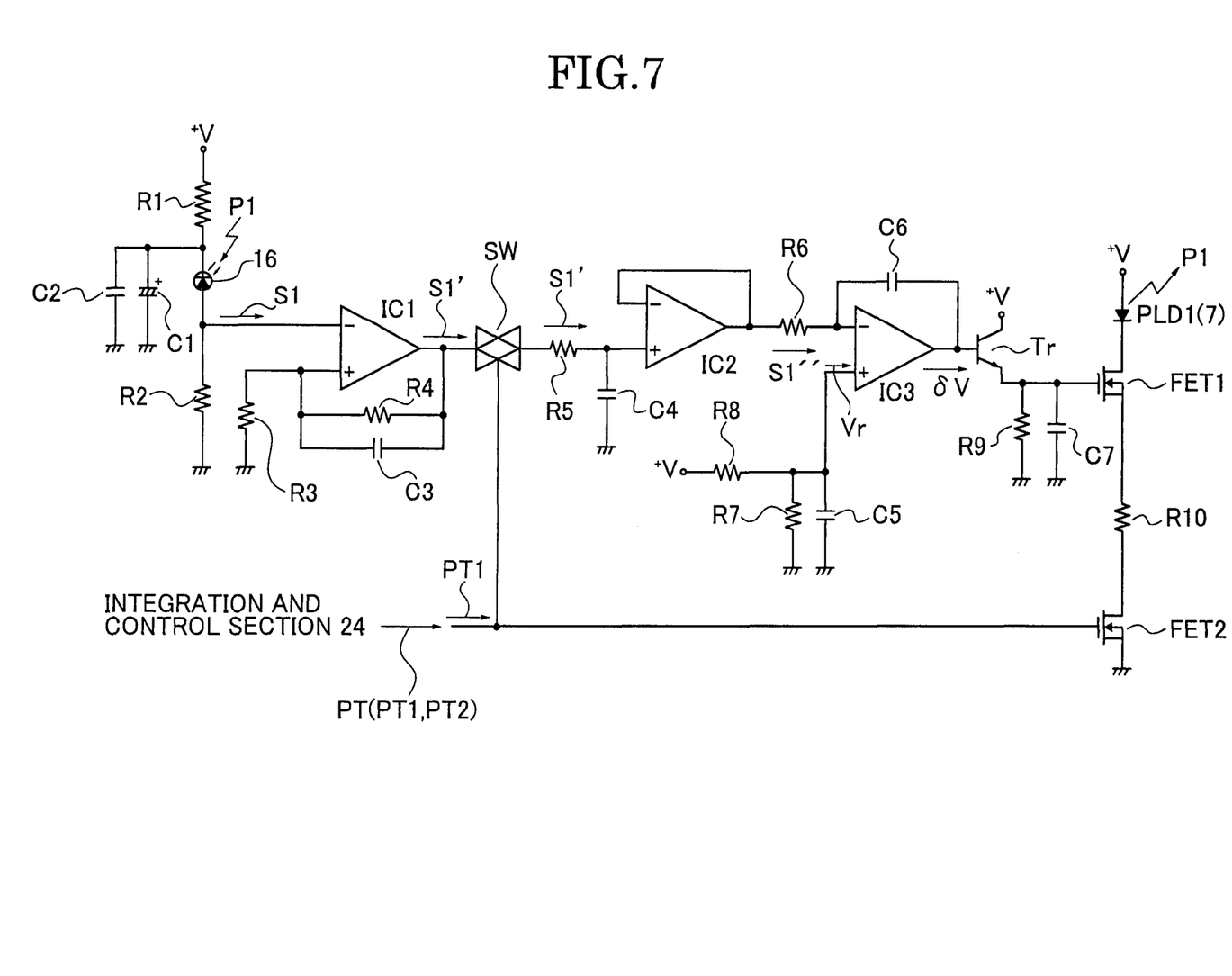
FIG. 7 provides a circuit view illustrating a detailed structure of a control circuit which controls light-emitting intensity and an emission timing of measuring light of a first light emitter.

FIG. 7 provides a circuit view illustrating the detailed structure of the controller for controlling the first light-emitting intensity controller (feedback circuit 19), which controls the light-emitting intensity of the measuring light P1 of the first light emitter 9 to become constant, and also the light-emitting timing of the measuring light P1.

Voltage +V is applied to the cathode of the photodiode 16 via a resistance R1. The connecting point between the resistance R1 and the cathode of the photodiode 16 is grounded via a capacitor C1. A capacitor C2 is connected to the capacitor C1 in parallel. The anode of the photodiode 16 is grounded via a resistance R2.

The connecting point between the anode of the photodiode 16 and the resistance R2 is connected to the negative input terminal of an operational amplifier (hereinafter, referred to as an Op-Amp) IC1. The positive input terminal of the Op-Amp IC1 is grounded via a resistance R3.

The output terminal of the Op-Amp IC1 is connected to the positive input terminal of the Op-Amp IC1 via a feedback resistance R4. A capacitor C3 is connected to the feedback resistance R4 in parallel.

The Op-Amp IC1 amplifies the pulse-like light-receiving signal S1 of the photodiode 16, and outputs the pulse-like light-receiving signal S1' in corporation with the resistances R1-R4 and the capacitors C1-C3.

The output terminal of the Op-Amp IC1 is connected to the positive input terminal of an Op-Amp IC2 via an analogue switching element SW and a resistance R5. The connecting point between the positive input terminal of the Op-Amp IC2 and the resistance R5 is grounded via a capacitor C4.

The output terminal of the Op-Amp IC2 is connected to the negative input terminal of the Op-Amp IC2, and also connected to the negative input terminal of an Op-Amp IC3 via a resistance R6.

The analogue switching element SW is turned on if the after-described pulse PT1 is input, and has a function which outputs the amplified pulse-like light-receiving signal S1' to the positive input terminal of the Op-Amp IC2.

The Op-Amp IC2 smoothes the pulse-like light-receiving signal S1' in cooperation with the resistance R5, the capacitor C4, and the resistance R6, and has a function which outputs the smoothed pulse-like light-receiving signal S1' as an analogue-like light-receiving signal S1' to the negative input terminal of the Op-Amp IC3.

The positive input terminal of the Op-Amp IC3 is grounded via a capacitor C5. A resistance R7 is connected to the capacitor C5 in parallel. Voltage V is applied to the connecting point between the positive input terminal of the Op-Amp IC3 and the capacitor C5 via a resistance R8.

The output terminal of the Op-Amp IC3 is connected to the negative input terminal of this Op-Amp IC3 via a capacitor C6, and also is connected to the base of a transistor Tr. Voltage V is applied to the collector of the transistor Tr. The emitter of the transistor Tr is connected to the gate of a field-effect transistor FET1, and also is grounded via a resistance R9. A capacitor C7 is connected to the resistance R9 in parallel.

The drain of the field-effect transistor FET1 is connected to the cathode of the laser diode PLD1 as the first light emitter 9. Voltage V is applied to the anode of the laser diode PLD1 as the first light emitter 9. The source of the field-effect transistor FET1 is connected to the drain of a field effect transistor FET2 via a resistance R10. The source of the field-effect transistor FET2 is grounded.

The Op-Amp IC3 compares the output voltage from the output terminal of the Op-Amp IC2 to the reference voltage Vr, and outputs the difference voltage 6V between the output voltage and the reference voltage Vr toward the base of the transistor Tr from the output terminal of the Op-Amp IC3.

The transistor Tr controls the gate voltage of the field-effect transistor FET 1 according to the difference voltage 6V such that the light-emitting intensity of the measuring light P1 to be irradiated from the photodiode PLD1 as the first light emitter 9 becomes constant.

The Op-Amp IC3, the transistor Tr, the resistances R7-R9, and the capacitors C5-C7 constitute a feedback circuit 21.

If the power source of the plant sensor is turned on, for example, the integration and control section 24 generates a periodic pulse PT having a constant width. The periodic pulse PT is input to the analogue switching element SW and the gate of the field-effect transistor FET2. By the field-effect transistor FET2 being periodically turned on or off, current periodically flows through the photodiode PLD1 as the first light emitter 9 in the arrow direction. Thereby, the first light emitter 9 periodically emits light, i.e., the measuring light P1 from the first light emitter 9 is pulsed light.

Figure 8A:
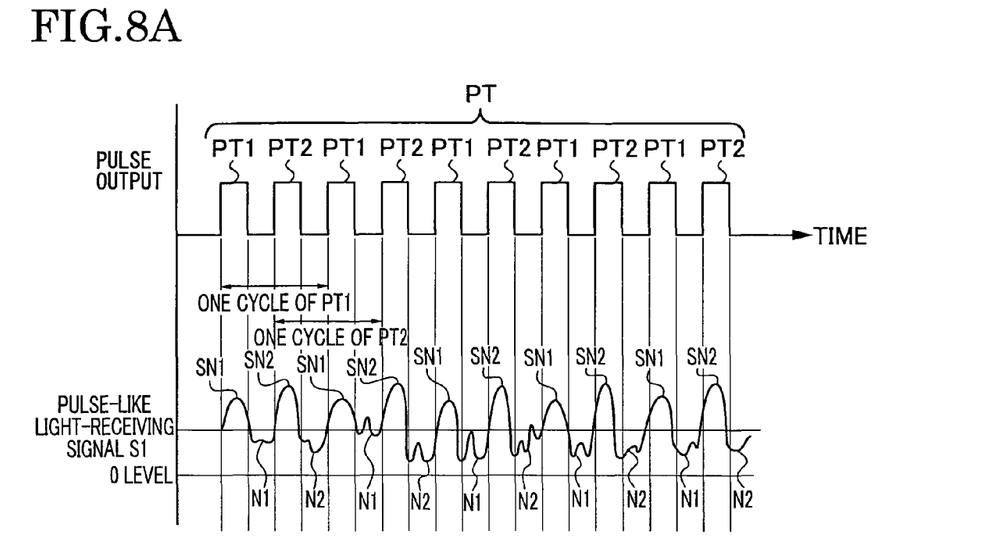

FIG. 8A illustrates one example of the periodic pulse PT. The periodic pulse PT includes a pulse PT1 which makes the first light emitter 9 periodically emit light and a pulse PT2 which makes the second light emitter 10 periodically emit light. The periodic pulse PT1 and the periodic pulse PT2 are alternatively generated. The time width of the periodic pulse PT1 is the same as the time width of the periodic pulse PT2. The time width of one cycle of the periodic pulse PT1 is also the same as the time width of one cycle of the periodic pulse PT2. In the embodiment of the present invention, the time width from the generation of the periodic pulse PT1 to the generation of the periodic pulse PT2 is the same as the time width from the generation of the periodic pulse PT2 to the generation of the next periodic pulse PT1.

Since a control circuit for controlling a second light-emitting intensity control circuit (feedback circuit 21), which controls the light-emitting intensity of the second measuring light P2 of the second light emitter 10 to become constant, and the emission timing of the measuring light P2, is the same as the control circuit for controlling the first light-emitting intensity control circuit (feedback circuit 19), which controls the light-emitting intensity of the first measuring light P1 of the first emitter 9 to become constant, and the emission timing of the measuring light P1, its detailed description will be omitted.

The CPU 13 also functions as a calculator which calculates, according to the integration signal output from the integration and control section 24, a reflection rate which is a ratio of the light intensity of the reflected light from the object to be measured 3 to the light intensity of the first measuring light P1, and also a reflection rate which is a ratio of the light intensity of the reflected light from the object to be measured 3 to the light intensity of the second measuring light P2, and obtains the information regarding the growing condition of the object to be measured 3.

In this case, the integration and control section 24 performs a first integration step which integrates the predetermined number of light-receiving signals SN1 as the pulse-like light receiving signals S1 including the component of the reflected light by the measuring light P1 in synchronization with the lighting of the light emitter 9, and outputs the integration signal, and also integrates the predetermined number of light-receiving signals SN2 as the pulse-like light-receiving signals S1 including the component of the reflected light by the measuring light P2 in synchronization with the lighting of the light emitter 10, and outputs the integration signal. The integration and control section 24 also performs a second integration step which integrates the predetermined number of light-receiving signals N1 as the pulse-like light-receiving signals S1 without having the component of the reflected light by the measuring light P1 in synchronization with the lighting-off of the light emitter 9, and outputs the integration signal, and also integrates the predetermined number of light-receiving signals N2 as the pulse-like light-receiving signals S1 without having the component of the reflected light from the measuring light P2 in synchronization with the lighting-off of the light emitter 10, and outputs the integration signal. After that, the integration and control section 24 outputs the integration signals to the CPU 13.

For instance, as illustrated in FIG. 8A, the light-receiving signals SN1, SN2 corresponding to the component of the light intensity containing the component of the reflected light by the measuring light P1, P2 and the component of the light intensity resulting from the ambient light are periodically and alternatively output from the light receiver 6.

Figure 8B:
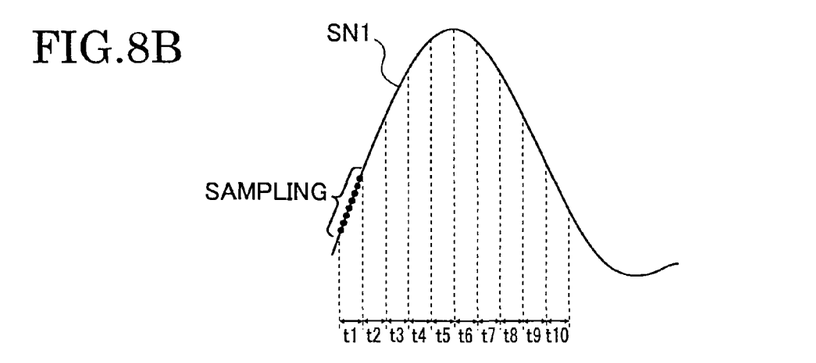
Figure 8C:
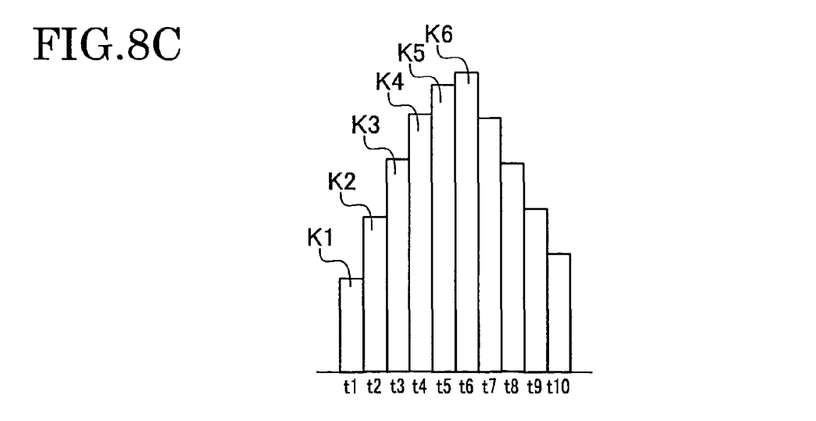

The integration and control section 24, for example, divides the pulse width of the light-receiving signal SN1 into ten intervals t1-t10 as illustrated in FIG. 8B, samples the light-receiving output for each of the intervals t1-t10, adds each of the sampling values, and temporarily stores the additional value. The integration and control section 24 samples the light-receiving output eight times at the interval t1, for example, and adds the eight sampling values, so as to obtain the additional value K1 as illustrated in FIG. 8C. After that, the integration and control section 24 temporarily stores this additional value K1.

The integration and control section 24 also performs the process for obtaining the additional values K2-K10, and obtains the peak value of the light-receiving signal SN1 from the additional values K1-K10. For example, in FIG. 8C, the peak value is the additional value K6.

Figure 9:
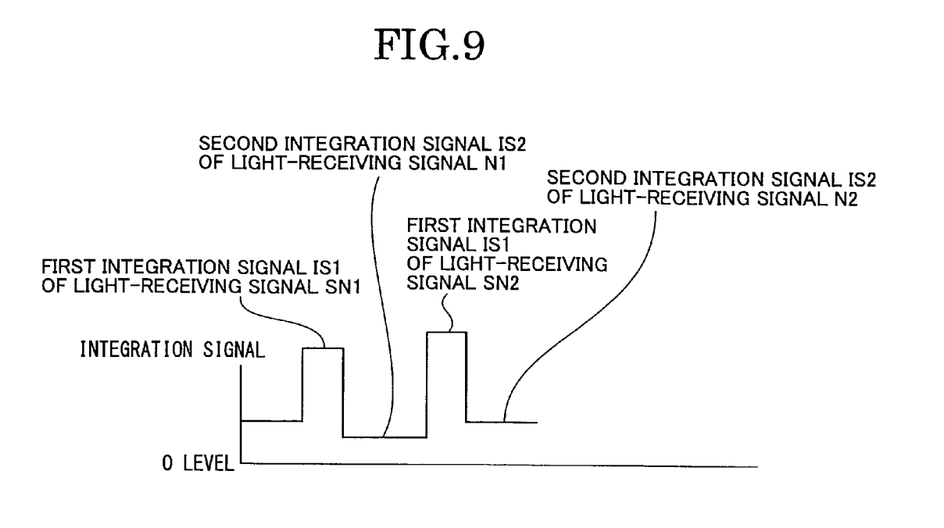
FIG. 9 provides an explanatory view of the output of integration signals of an integration section illustrated in FIG. 3.

If the predetermined number of peak values of the light-receiving signal SN1 is integrated, the integration signal IS1 in which the reflected light component by the measuring light P1 is emphasized is obtained as illustrated in FIG. 9.

In the similar way, the light-receiving signal SN2 is sampled, and the peak value of the light-receiving signal SN2 is obtained. Then, if the predetermined number of peak values of the light-receiving signal SN2 is integrated, the first integration signal IS1 in which the reflected light component by the measuring light P2 is emphasized is obtained as illustrated in FIG. 9.

The light-receiving signals N1, N2 are also sampled, and the peak values of the light-receiving signals N1, N2 are also obtained.

Moreover, in the similar way, if only the light-receiving signals N1, N2 are sampled in synchronization with the lighting-off of the light emitters 9, 10, respectively, the peak values are obtained, and the predetermined number of the peak values is integrated, the second integration signal IS2 resulting from only the ambient light without having the component of reflected light by the measuring light P1, P2 is obtained.

Figure 10:
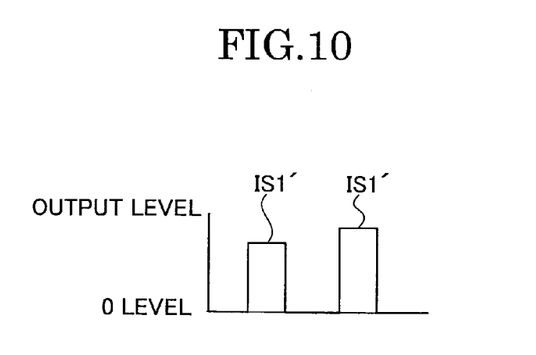
FIG. 10 provides an explanatory view of the output of integration signals from which noise is eliminated.

The calculator also includes a function which reduces (removes) the second integration signal IS2 obtained by the second integration step from the first integration signal IS1 obtained by the first integration step (i.e., the first integrated signal IS1 is reduced by the second integrated signal IS2). If the second integration signal IS2 is removed from the first integration signal IS1, only the light-receiving signal IS1' resulting from the component of the reflected light intensity from the object to be measured 3 can be extracted for each measuring light as illustrated in FIG. 10. Thereby, the information regarding the growing condition of the object to be measured 3 can be accurately extracted.

The information regarding the growing condition of the object to be measured 3 is output outside by an RS-232C driver circuit 26 or a CAN driver circuit 27 as data.

Data or a program necessary for driving the plant sensor is input to the CPU 13 by the driving circuit 26 or the CAN driver circuit 27. In addition, in FIG. 3, reference number 28 denotes an external power supplying source, and reference number 29 denotes a power source circuit. Necessary power is supplied to each circuit of the plant sensor from the power source circuit 29.

In the embodiment of the present invention, the light-emitting intensity of the measuring light P1 to be irradiated from the first light emitter 9 and the light-emitting intensity of the measuring light P2 to be emitted from the second light emitter 10 are controlled by the light-receiving intensity of the first auxiliary light receiver (photodiode 16) and the light-receiving intensity of the second auxiliary light receiver (photodiode 17), and the reflection rate is obtained by the total light-emitting intensity of the first and second light emitters 9, 10.

However, the plant sensor according to the embodiment of the present invention can be configured to include the light source section 4 having the first light emitter 9, which periodically emits the first measuring light P1 whose peak wavelength of the emission intensity is the first wavelength, and irradiates the first measuring light P1 toward the object to be measured 3, the second light emitter 10, which periodically emits the second measuring light P2 whose peak wavelength of the emission intensity is the second wavelength, and irradiates the second measuring light P2 toward the object to be measured 3, the light receiver 6, which receives the reflected light of each measuring light P1, P2 from the object to be measured 3, and outputs the light-receiving signals, and the first auxiliary light receiver (photodiode 16), which receives part of the measuring light P1 irradiated from the first light emitter 9. In addition, the plant sensor can include the control circuit, which controls the emission of the first light emitter 9 and the emission of the second light emitter 10 at a different timing, the integration and control section 24, which integrates the light-receiving signals output from the light receiver 6 in a predetermined time, and outputs the integration signal, and the calculator, which calculates, according to the integration signal from the integration and control section 24 and the light-receiving signals from the first auxiliary light receiver (photodiode 16), the reflection rate as the ratio of the light intensity of the reflected light of the first measuring light P1 from the object to be measured 3 to the light intensity of the first measuring light P1 of the first light emitter 9, and obtains the information regarding the growing condition of the object to be measured 3.

In this case, it is preferable for the light source section 4 to include the first temperature detector 11, which detects the temperature of the first light emitter 9, the first temperature adjuster, which adjusts the temperature of the first light emitter 9, and the first temperature control circuit, which controls the first temperature adjuster 7 according to the result of the first temperature detector 11 such that the temperature of the first light emitter 9 becomes constant.

It is more preferable for the light source section 4 to include the second temperature detector 12, which detects the temperature of the second light emitter 10, the second temperature adjuster 8, which adjusts the temperature of the second light emitter 10, and the second temperature control circuit, which controls the second temperature adjuster 8 according to the result of the second temperature detector 12 such that the temperature of the second light emitter 10 becomes constant.

It is more preferable for the light source section 4 to include the second auxiliary light receiver (photodiode 17), which receives part of the second measuring light P2 irradiated from the second light emitter 10, and for the calculator to calculate the reflection rate as the ratio of the light intensity of the reflected light of the measuring light P1, P2 from the object to be measured 3 to the light intensity of the irradiation light of the second light emitter 10 according to the integration signal output from the integration and control section 24 and the light-receiving signal of the second auxiliary light receiver (photodiode 17).

Moreover, in the embodiment of the present invention, it is described that the light-emitting unit 5 includes two light emitters of the first and second light emitters 9, 10 However, the number of light emitters is not limited thereto, and three light emitters or more for irradiating measuring light whose peak wavelengths of emission intensity are different from each other can be used for the light-emitting unit 5.

According to the embodiment of the present invention, the influence of light intensity component resulting from the ambient light can be reduced while simplifying the structure.

In addition, since at least two measuring lights whose peak wavelengths of the emission intensity are different from each other are emitted at a different emission timing of each light emitter, and the reflection rate is obtained for each measuring light by integrating the light-receiving signals output from the light receiver, the integration can be performed by using the identical integrator although the reflection rate of the object to be measured is obtained for each measuring light by using at least two measuring lights whose peak wavelengths of emission intensity are different from each other.

For example, if the number of times which integrates the light-receiving signals from the light receiver is significantly increased, the component of the light intensity resulting from the ambient light can be relatively reduced. As a result, the reflection rate of the object to be measured can be further accurately measured while simplifying the structure of the optical system.

Especially, in the plant sensor according to the embodiment of the present invention, the integrator performs the first integration step, which integrates for each wavelength the light-receiving signals containing the component of the reflected light of the measuring light from the object to be measured in synchronization with the lighting of each light emitter, and outputs the integration signal, and the second integration step, which integrates the light-receiving signals without having the component of the reflected light of each measuring light from the object to be measured in synchronization with the lighting-off of each light emitter, and outputs the integration signal. After that, the calculator removes the integration signal obtained by the second integration step from the integration signal obtained from the first integration step. Accordingly, the reflection rate of the object to be measured can be further accurately measured.

It is preferable for the light source section to include the first auxiliary light receiver, which receives part of the light intensity of the first measuring light irradiated toward the object to be measured from the first light emitter, and the first light-emitting intensity controller, which controls the light intensity of the first measuring light of the first light emitter to become constant according to the light-receiving signal of the first auxiliary light receiver.

It is also preferable for the light source section to include the second auxiliary light receiver, which receives part of the light intensity of the second measuring light irradiated toward the object to be measured from the second light emitter, and the second light-emitting intensity controller, which controls the light-intensity of the second measuring light of the second light emitter to become constant according to the light-receiving signal of the second auxiliary light receiver.

By the above-described structures, the light intensity of each measuring light to be emitted from each light emitter can be constantly maintained, and the reflection rate of each measuring light of the object to be measured, i.e., the reflection rate for each wavelength can be further accurately measured.

It is preferable for the light source section to include the first temperature detector, which detects the temperature of the first light emitter, the first temperature adjuster, which adjusts the temperature of the first light emitter, and the first temperature control circuit, which controls the first temperature adjuster according to the result of the first temperature detector such that the temperature of the first light emitter becomes constant.

It is also preferable for the light source section to include the second temperature detector, which detects the temperature of the second light emitter, the second temperature adjuster, which adjusts the temperature of the second light emitter, and the second temperature control circuit, which controls the second temperature adjuster according to the result of the second temperature detector such that the temperature of the second light emitter becomes constant.

By the above-described structure, the peak wavelength of emission intensity of the measuring light to be emitted from each light emitter can be constantly maintained, and also the light-emitting intensity can be constantly maintained. Therefore, the reflection rate of the object to be measured can be further accurately measured.

It is preferable for the light source to include the first temperature detector, which detects the temperature of the first light emitter, the first temperature adjuster, which adjusts the temperature of the first light emitter, the first temperature control circuit, which controls the first temperature adjuster according to the result of the first temperature detector such that the temperature of the first light emitter becomes constant, the second temperature detector, which detects the temperature of the second light emitter, the second temperature adjuster, which adjusts the temperature of the first light emitter and the temperature of the second light emitter, and the second temperature control circuit, which controls the second temperature adjuster according to the result of the second temperature detector such that the temperature of the first light emitter and the temperature of the second light emitter become constant.

In this case, it is preferable for the first and second light emitters to be the pulsed oscillation laser diode, for the first and second temperature adjusters to be the Peltier effect element, and for the temperature of the first light emitter to be adjusted by the second temperature adjuster via the first temperature adjuster.

By the above-described structure, the temperature of the first light emitter can be roughly adjusted by the second temperature adjuster, and the temperature of the first light emitter can be precisely adjusted by the first temperature adjuster. Therefore, the temperature can be smoothly and accurately adjusted.

Moreover, if the wavelength variation of the measuring light in the wavelength area portion in which the change of the reflection rate of the object to be measured is large relative to the wavelength is controlled by setting the peak wavelength of the emission intensity of the first measuring light to the red wavelength (733 nm) and the peak wavelength of the second measuring light to the near-infrared wavelength (808 nm), the normalized difference vegetation index {(reflection rate of near-infrared wavelength−reflection rate of red wavelength)/ (reflection rate of near-infrared wavelength+reflection rate of red wavelength)}, which appropriately indicates the growing condition of the object to be measured, can be accurately obtained.

According to the embodiment of the present invention, it is preferable for the light source section to include the first temperature detector, which detects the temperature of the first light emitter, the first temperature adjuster, which adjusts the temperature of the first light emitter, and the first temperature control circuit, which controls the first temperature adjuster according to the result of the first temperature detector such that the temperature of the first light emitter becomes constant.

In this case, it is preferable for the light source section to include the second temperature detector, which detects the temperature of the second light emitter, the second temperature adjuster, which adjusts the temperature of the second light emitter, and the second temperature control circuit, which controls the second temperature adjuster according to the result of the second temperature detector such that the temperature of the second light emitter becomes constant.

It is also preferable for the light source section to include the second auxiliary light receiver, which receives part of the second measuring light irradiated from the second light emitter, and for the calculator to calculate the reflection rate as the ratio of the light intensity of the reflected light from the object to be measured to the light intensity of the second measuring light according to the integration signal from the integrator and the light-receiving signal of the second auxiliary light receiver.

As described above, although the present invention has been described in terms of the embodiment, it is not limited thereto. It should be appreciated that variations may be made in the embodiment described by persons skilled in the art without departing from the scope of the present invention as defined by the following claims.

What is claimed is:

1. A plant sensor, comprising:
   a light source section, including:
   a first light emitter configured to periodically emit first measuring light whose peak wavelength of emission intensity is a first wavelength, and to irradiate the first measuring light toward an object to be measured;
   a second light emitter configured to periodically emit second measuring light whose peak wavelength of emission intensity is a second wavelength, and to irradiate the second measuring light toward the object to be measured; and
   a light receiver configured to receive reflected light of each of the first measuring light and the second measuring light from the object to be measured, and output light-receiving signals;

a controller configured to control emission of the first light emitter and emission of the second light emitter at different timings;

an integrator configured to integrate the light-receiving signals by performing a first integration step comprising integration of the light-receiving signals including a component of the reflected light of each of the measuring light from the object to be measured in synchronization with lighting of each of the light emitters and outputting a first integration signal, and by performing a second integration step comprising integration of the light-receiving signals without having the component of the reflected light of each of the measuring light from the object to be measured in synchronization with lighting-off of the each of the light emitters and outputting a second integration signal; and a calculator configured to calculate, according to the first integration signal and the second integration signal from the integrator, a reflection rate as a ratio of light intensity of the reflected light of the first measuring light from the object to be measured to light intensity of the first measuring light, and a reflection rate as a ratio of light intensity of the reflected light of the second measuring light from the object to be measured to light intensity of the second measuring light, to obtain information regarding a growing condition of the object to be measured, and to reduce the first integration signal obtained by the first integration step by the second integration signal obtained by the second integration step.

2. The plant sensor according to claim 1, wherein
the light source section includes a first auxiliary light receiver configured to receive part of light intensity of the first measuring light to be irradiated to the object to be measured from the first light emitter, and a first light-emitting volume controller configured to control the light intensity of the first measuring light to become constant according to a light-receiving signal of the first auxiliary light receiver.

3. The plant sensor according to claim 2, wherein
the light source section further includes a second auxiliary light receiver configured to receive part of a light intensity of the second measuring light to be irradiated to the object to be measured from the second light emitter, and a second light-emitting volume controller configured to control the light intensity of the second measuring light to become constant according to a light-receiving signal of the second auxiliary light receiver.

4. A plant sensor, comprising:
a light source section, including:
a first light emitter configured to periodically emit first measuring light whose peak wavelength of emission intensity is a first wavelength, and to irradiate the first measuring light toward an object to be measured;
a second light emitter configured to periodically emit second measuring light whose peak wavelength of emission intensity is a second wavelength, and to irradiate the second measuring light toward the object to be measured; and
a light receiver configured to receive reflected light of each of the first measuring light and the second measuring light from the object to be measured, and output light-receiving signals;
a controller configured to control emission of the first light emitter and emission of the second light emitter at different timings;
an integrator configured to integrate the light-receiving signals, and output an integration signal; and a calculator configured to calculate, according to the integration signal from the integrator, a reflection rate as a ratio of light intensity of the reflected light of the first measuring light from the object to be measured to light intensity of the first measuring light, a reflection rate as a ratio of light intensity of the reflected light of the second measuring light from the object to be measured to light intensity of the second measuring light, and obtain information regarding a growing condition of the object to be measured;

wherein the light source section further includes a first temperature detector configured to detect a temperature of the first light emitter, a first temperature adjuster configured to adjust the temperature of the first light emitter, and a first temperature control circuit configured to control the first temperature adjuster according to a result of the first temperature detector such that the temperature of the first light emitter becomes constant.

5. The plant sensor according to claim 3, wherein
the light source section further includes a second temperature detector configured to detect a temperature of the second light emitter, a second temperature adjuster configured to adjust the temperature of the second light emitter, and a second temperature control circuit configured to control the second temperature adjuster according to a result of the second temperature detector such that the temperature of the second light emitter becomes constant.

6. The plant sensor according to claim 4, wherein
the light source section further includes a second temperature detector configured to detect a temperature of the second light emitter, a second temperature adjuster configured to adjust the temperature of the first light emitter and the temperature of the second light emitter, and a second temperature control circuit configured to control the second temperature adjuster according to a result of the second temperature detector such that the temperature of the first light emitter and the temperature of the second light emitter become constant.

7. The plant sensor according to claim 6, wherein
each of the first light emitter and the second light emitter is a pulsed oscillation laser diode, each of the first temperature adjuster and the second temperature is a Peltier effect element, and the temperature of the first light emitter is adjusted by the second temperature adjuster via the first temperature adjuster.

8. A plant sensor, comprising:
a light source section, including:
a first light emitter configured to periodically emit first measuring light whose peak wavelength of emission intensity is a first wavelength, and to irradiate the first measuring light toward an object to be measured;
a second light emitter configured to periodically emit second measuring light whose peak wavelength of emission intensity is a second wavelength, and to irradiate the second measuring light toward the object to be measured;
a light receiver configured to receive reflected light of each of the first measuring light and the second measuring light from the object to be measured, and output light-receiving signals; and
a first auxiliary light receiver configured to receive part of the first measuring light irradiated from the first light emitter;
a controller configured to control emission of the first light emitter and emission of the second light emitter at different timings;

an integrator configured to integrate the light-receiving signals by performing a first integration step comprising integration of the light-receiving signals including a component of the reflected light of each of the measuring light from the object to be measured in synchronization with lighting of each of the light emitters and outputting a first integration signal, and by performing a second integration step comprising integration of the light-receiving signals without having the component of the reflected light of each of the measuring light from the object to be measured in synchronization with lighting-off of the each of the light emitters and outputting a second integration signal; and a calculator configured to calculate, according to the first integration signal and the second integration signal from the integrator and a light-receiving signal from the first auxiliary light receiver, a reflection rate as a ratio of light intensity of the reflected light of the first measuring light from the object to be measured to light intensity of the first measuring light, to obtain information regarding a growing condition of the object to be measured, and to reduce the first integration signal obtained by the first integration step by the second integration signal obtained by the second integration step.

9. The plant sensor according to claim 8, wherein the light source section further includes a first temperature detector configured to detect a temperature of the first light emitter, a first temperature adjuster configured to adjust the temperature of the first light emitter, and a first temperature control circuit configured to control the first temperature adjuster according to a result of the first temperature adjuster such that the temperature of the first light emitter becomes constant.

10. The plant sensor according to claim 9, wherein the light source section further includes a second temperature detector configured to detect a temperature of the second light emitter, a second temperature adjuster configured to adjust the temperature of the second light emitter, and a second temperature control circuit configured to control the second temperature adjuster according to a result of the second temperature detector such that the temperature of the second light emitter becomes constant.

11. The plant sensor according to claim 9, wherein the light source section further includes a second auxiliary light receiver configured to receive part of the second measuring light irradiated from the second light emitter, and the calculator calculates a reflection rate as a ratio of light intensity of the reflected light of the second measuring light from the object to be measured to light intensity of the second measuring light according to the integration signal from the integrator and a light-receiving signal of the second auxiliary light receiver.

* * * * *